United States Patent

Perego et al.

Patent Number: 5,625,108
Date of Patent: Apr. 29, 1997

[54] PROCESS FOR PREPARING AMORPHOUS, CATALYTICALLY ACTIVE SILICOALUMINAS

[75] Inventors: Carlo Perego; Stefano Peratello; Roberto Millini, all of Milan, Italy

[73] Assignees: Eniricerche S.p.A., Milan; AGIP Petroli S.p.A., Rome; Enichem Synthesis S.p.A., Palermo, all of Italy

[21] Appl. No.: 457,814

[22] Filed: Jun. 1, 1995

Related U.S. Application Data

[62] Division of Ser. No. 361,581, Dec. 22, 1994.

[30] Foreign Application Priority Data

Dec. 22, 1993 [IT] Italy .................... MI93A2696

[51] Int. Cl.$^6$ .................................... C07C 2/02
[52] U.S. Cl. ............... 585/520; 585/530; 585/531; 585/532; 585/533
[58] Field of Search .................. 585/520, 530, 585/531, 532, 533

[56] References Cited

U.S. PATENT DOCUMENTS 5,444,032  8/1995  Perego et al. .

FOREIGN PATENT DOCUMENTS 0340868  11/1989  European Pat. Off. .

*Primary Examiner*—Glenn A. Caldarola
*Assistant Examiner*—E. D. Irzinski
*Attorney, Agent, or Firm*—Oblon, Spivak, McClelland, Maier & Neustadt, P.C.

[57] ABSTRACT

An amorphous, micro/mesoporous silica-alumina gel with controlled pore size, having a surface area of at least 500 $m^2/g$ and with a molar ratio of $SiO_2:Al_2O_3$ of at least 30:1, is prepared by hydrolysing and causing a tetra-alkyl ammonium hydroxide, an aluminum trialkoxide, and a tetra-alkyl orthosilicate to gelate, by operating at a temperature equal to, or higher than, the boiling temperature, under atmospheric pressure, of any alcohols which are developed as a by-product from said hydrolysis reaction, without said alcohols being removed, or being substantially removed, from the reaction media; and the so produced gel being dried and fired. So obtained gel is an active catalyst in hydrocarbon conversion reactions, in particular in light olefin isomerization and oligomerization processes, e.g., in propylene oligomerization processes to yield useful liquid hydrocarbons for gasoline and jet fuel formulation.

15 Claims, 5 Drawing Sheets

5,625,108

PROCESS FOR PREPARING AMORPHOUS, CATALYTICALLY ACTIVE SILICOALUMINAS

This is a division of application Ser. No. 08/361,581 filed on Dec. 22, 1994.

TITLE OF THE INVENTION

BACKGROUND OF THE INVENTION

1. Field of the Invention

The present invention relates to a process for preparing an amorphous and micro/mesoporous silica-alumina gel having a large surface area and a controlled pore size, which is catalytically active in hydrocarbon conversion reactions.

2. Discussion of the Background

Some silica and alumina gels displaying catalytic activity are known in the art. So, e.g., EP-A-160 145 discloses a process for alkylating aromatic hydrocarbons using, as the catalyst, a silica/alumina gel of amorphous character with a diameter of the pores typically of 50–500 Ångstroms and with a molar silica:alumina ratio typically comprised within the range of from 1:1 to 10:1.

Furthermore, R. M. S. Malton and J. Davidtz in Journal of Catalysis, 60, 156–166 (1979) disclose a process for the synthesis of amorphous silica and alumina catalysts, with a controlled pore volume.

Finally, U.S. Pat. No. 5,049,536 discloses a microporous, x-ray amorphous silica/alumina gel having a surface area of from 500 to 1000 m$^2$/g and a pore volume comprised within the range of from 0.3 to 0.6 cm$^3$/g. Such a silica and alumina gel, which is catalytically active in hydrocarbon preparation reactions, is typically prepared by hydrolysing a tetra-alkyl ammonium hydroxide, a hydrolysable aluminum compound and a hydrolysable silicon compound and causing the resulting hydrolysis mixture to undergo gelation by operating in an aqueous media and at low temperatures, and then submitting the resulting gel to drying and firing.

SUMMARY OF THE INVENTION

The present Applicants found now, according to the present invention, that, in relation with U.S. Pat. No. 5,049,036, special conditions exist for the hydrolysis of the above mentioned reactants and subsequent gelation which make it possible to obtain a silica-alumina gel which is unexpectedly improved in terms of control of its surface characteristics, in particular its porous structure, as well as in terms of its catalytic performance, in particular its activity and useful life time under use conditions.

DETAILED DESCRIPTION OF THE PREFERRED EMBODIMENTS

Figure 1:
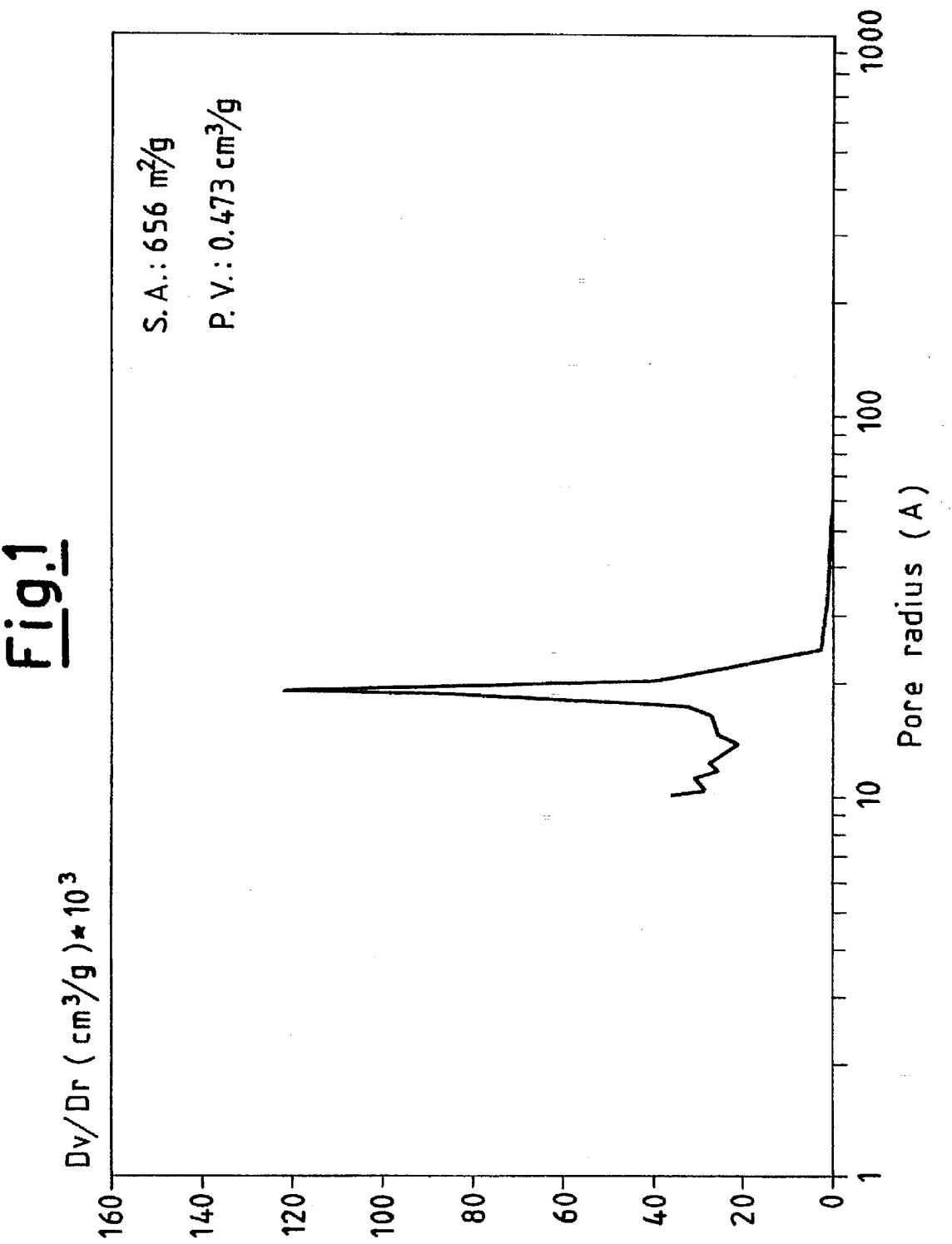

In accordance therewith, the present invention relates to a process for preparing an amorphous, micro/mesoporous silica-alumina gel with controlled pore size, having a surface area of at least 500 m$^2$/g and with a molar ratio of SiO$_2$:Al$_2$O$_3$ of at least 30:1, by starting from a tetra-alkyl ammonium hydroxide, an aluminum compound capable of yielding Al$_2$O$_3$ by hydrolysis (i.e., hydrolysable to Al$_2$O$_3$), and a silicon compound capable of yielding SiO$_2$ by hydrolysis (i.e., hydrolysable to SiO$_2$), characterized in that:

said tetra-alkyl ammonium hydroxide is a tetra-($C_2$-$C_5$)-alkyl ammonium hydroxide, said hydrolysable aluminum compound is an aluminum tri-($C_2$-$C_4$)-alkoxide and said hydrolysable silicon compound is a tetra-($C_1$-$C_4$)-alkyl orthosilicate, and said reactants are submitted to hydrolysis and gelation, by operating at a temperature equal to, or higher than, the boiling temperature, under atmospheric pressure, of any alcohol which is developed as a by-product from said hydrolysis reaction, without said alcohols being removed, or being substantially removed, from the reaction media; and the so produced gel is dried and fired.

The useful tetra-alkyl ammonium hydroxide for the purposes of the present invention is therefore selected from tetraethyl-, propyl-, isopropyl-, butyl-, isobutyl-, t-butyl-, and pentyl-ammonium hydroxide, and among these, tetrapropyl-, tetraisopropyl- or tetrabutyl-ammonium hydroxide are preferred.

Aluminum trialkoxide is selected from aluminum triethoxide, propoxide, isopropoxide, butoxide, isobutoxide and t-butoxide. Among these, aluminum tri-propoxide and tri-isopropoxide are preferred.

Tetra-alkyl orthosilicate is selected from tetra- methyl-, tetraethyl-, propyl-, isopropyl-, butyl-, isobutyl-, t-butyl- and pentyl-orthosilicate and among these, tetra-ethyl orthosilicate is preferred.

The process according to the present invention is carried out by first preparing an aqueous solution containing tetra-alkyl ammonium hydroxide and aluminum tri-alkoxide, by operating at a high enough temperature in order to secure that the aluminum compound will be properly dissolved. To said aqueous solution, tetra-alkyl orthosilicate is then added. The resulting mixture is then heated up to a suitable temperature for starting the hydrolysis reaction. Said temperature is a function of the composition of the reaction mixture (comprised within the range of from 70° to 100° C). The hydrolysis reaction is an exothermic one and therefore once that the reaction is started, its self-feeding is secured. The amounts of the reactants which constitute the reaction mixture should furthermore be such as to comply with the molar ratios: SiO$_2$:Al$_2$O$_3$ comprised within the range of from 30:1 to 500:1, tetra alkyl ammonium hydroxide:SiO$_2$ comprised within the range of from 0.05:1 to 0.2:1 and H$_2$O:SiO$_2$ comprised within the range of from 5:1 to 40:1. Preferred values for these molar ratios are: SiO$_2$:Al$_2$O$_3$ from 50:1 to 300:1; tetra-alkyl ammonium hydroxide: SiO$_2$ from 0.05:1 to 0.2:1 and H$_2$O:SiO$_2$ from 10:1 to 25:1.

As said above, the basic aspect of the process of the present invention is that the hydrolysis of the reactants and their gelation is carried out by operating at a temperature equal to, or higher than, the boiling temperature, under atmospheric pressure, of any alcohols which are developed as a by-product from said hydrolysis reaction, without said alcohols being removed, or substantially removed, from the reaction media. Therefore, the hydrolysis/gelation temperature is critical and will be properly kept comprised within the range of from about >65° C. up to about 110° C. Furthermore, in order to keep any developed alcohols retained in the reaction media, the process can be carried out in an autoclave under the autogenous system pressure at the selected operating temperature (normally of the order of 1.1–1.5 abs.bars), or the process can be carried out under atmospheric pressure inside a reactor equipped with a reflux condenser.

According to a particular embodiment of the process, the hydrolysis and gelation are carried out in the presence of a larger alcohol amount than as developed as a reaction by-product. For this purpose, a free alcohol, and preferably ethanol, is added to the reaction mixture up to a maximal value of molar ratio of added alcohol:SiO$_2$, of 8:1.

The necessary time in order to cause the hydrolysis and gelation to reach their completion, under the above shown conditions, is normally comprised within the range of from 10 minutes to 3 hours, and preferably is of the order of 1–2 hours.

It was furthermore found it useful to submit the resulting gel to ageing, by keeping the hydrolysis/gelation mixture in the presence of the alcohol and under room temperature conditions for a time of the order of from 1 to 24 hours.

Finally, the alcohol is removed from the gel, and the Latter is dried under vacuum (e.g., under a vacuum of 30 torr), at a temperature of 110° C. The dried gel is finally fired under an oxidizing atmosphere (normally atmospheric air) at a temperature comprised within the range of from 500° to 700° C. during a time period of from 4 to 20 hours, and preferably at 500°–600° C. during 6–10 hours.

The so obtained silica-alumina gel shows a composition which corresponds to the composition of the starting reactants, considering that the reaction yields are practically quantitative. Therefore, the molar ratio of $SiO_2:Al_2O_3$ will be comprised within the range of from 30:1 to 500:1 and preferably of from 50:1 to 300:1, with most preferred values being of the order of 100:1.

When it is analysed by powder x-ray diffractometry, this gel results to be amorphous; it displays a surface area of at least 500 $m^2/g$ and normally comprised within the range of from 600 to 850 $m^2/g$ and a pore volume of 0.4–0.8 $cm^3/g$. Finally, it was found that by means of the process of the present invention, the size of the pores can be controlled to be within a certain range of values, and in particular within the range of from 10 to about 20 Ångstroms (values referred to pore radius), with, in particular, said pores showing a narrow size distribution, as it will be clearer from the experimental examples reported in the following.

The gel obtained according to the present process is an active catalyst in the usual reactions of conversion of hydrocarbons, like light olefin isomerization and oligomerization reactions.

The gel is particularly useful in propylene oligomerization, to yield hydrocarbon cuts, liquid under room conditions, which are constituted by branched olefin oligomers useful for gasoline or jet fuel formulation.

The following Examples are reported in order to better illustrate the invention.

EXAMPLE 1

In this Example, the process according to the present invention is carried out with the following molar ratios of the components of the starting reaction mixture:

| | | |
|---|---|---|
| $SiO_2:Al_2O_3$ | = | 100 |
| TPA—OH:$SiO_2$ | = | 0.09 |
| $H_2O:SiO_2$ | = | 15 |

An amount of 4,727 g of water and 3,922 g of TPA-OH (tetra-propyl ammonium hydroxide; used as a solution at 14% by weight in water) are charged to an autoclave of 20 liters of capacity.

The solution in the autoclave is heated and when the temperature reaches 60° C., 120 g of Al(OiPr)$_3$ (aluminum isopropoxide; supplied by Fluka) is added.

The autoclave is closed, stirring is started, and the reaction mixture is kept at the above temperature during the necessary time for aluminum compound to be completely dissolved (about 40 minutes). Now, the temperature of the autoclave is increased up to 90° C., and 6,250 g of TEOS (tetra-ethyl orthosilicate) is added through a purposely provided valve. When addition is complete, the valve is closed, the temperature is adjusted at 88° C. and the autoclave is kept under said conditions during 3 hours. The pressure reading on the pressure gauge reaches the maximal value of 1.5 bars.

A thick liquid product is thusly obtained which, after being aged during approximately 12 hours, is dried inside a rotary dryer, under vacuum (about 60 torr) and is then calcined in air at 550° C. for about 8 hours.

The analysis by powder x-ray diffractometry [carried out by means of a Philips Vertical Diffractometer equipped with proportional pulse counter and operating with Cu K-α radiation (lambda=1.54178Å)], indicates that the calcined solid product is amorphous.

The specific surface area of said solid product [as determined by BET analysis by $N_2$ adsorption at liquid $N_2$ temperature (77° K.) with a Carlo Erba Sorptomatic 1900 apparatus] resulted to be of 656 $m^2/g$.

The specific pore volume [as determined by $N_2$ adsorption/desorption cycles at 77° K., using a Carlo Erba Sorptomatic 1900 apparatus] is of 0.473 $cm_3/g$, with the pore size distribution being as shown in FIG. 1.

By adopting the terms suggested by IUPAC Manual of Symbols and Terminology, Appendix 2, Part I Coll., Surface Chem. Pure Appl. Chem., 31, 578 (1972), according to which those pores having a diameter of <20Å are defined as "micropores" and those pores having a diameter comprised within the range of from 20Å to 500Å are defined as "mesopores", the solid product obtained according to the present invention can be defined as being a "micro/mesoporous" material.

In following Table 1, the data are reported of catalytic activity in propylene oligomerization reaction, operating with a WHSV (weight hourly space velocity) value of 4 h$^{-1}$, and under a 35-bar pressure.

In this Table, as well as in following tables, the term "T.O.S." means "Time On Stream", i.e., the cumulated run time expressed as hours, and "Conversion (%)" is the calculated conversion rate based on fed propylene.

TABLE 1

| T.O.S. | Temperature (°C.) | Conversion (%) |
|---|---|---|
| 42 | 140 | 65 |
| 63 | 150 | 67 |
| 134 | 190 | 67 |

The process is carried out by operating according to Example 1, in a 5-liter autoclave, to which the following amounts of reactants are charged:

| | | |
|---|---|---|
| $H_2O$ | = | 1,182 g |
| TPA—OH | = | 980 g |
| Al(OiPr)$_3$ | = | 30 g |
| TEOS | = | 1,560 g |

The end product obtained from this test run results to be amorphous when analysed by powder x-ray diffractometry; it has a BET surface area of 710 $m^2/g$, and a pore volume of 0.596 $cm^3/g$.

In following Table 2, the data are reported of catalytic activity in propylene oligomerization reaction, operating with a WHSV value of 4 h$^{-1}$ and under a 35-bar pressure.

TABLE 2

| T.O.S. | Temperature (°C.) | Conversion (%) |
|---|---|---|
| 20 | 120 | 77 |
| 63 | 140 | 77 |
| 133 | 160 | 57 |

EXAMPLE 3

In this Example, the process is carried out in a 1-liter autoclave, with the following molar ratios of the components of the reaction mixture:

| $SiO_2:Al_2O_3$ | = | 100 |
|---|---|---|
| TPA—OH:$SiO_2$ | = | 0.09 |
| $H_2O:SiO_2$ | = | 15 |

From 158 g of water, 131 g of TPA-OH (used an a solution at 14% by weight in water) and 4 g of Al(OiPr)$_3$ a solution is prepared on a heater plate at 60° C. When the aluminum salt is dissolved, the solution is charged to a 1-liter autoclave previously thermostatted at 60° C., through a pin valve.

Now, the temperature of the solution is increased up to about 85° C., and, still through the pin valve, 208 g of TEOS is added.

When the hydrolysis reaction is complete, the reaction mixture is kept at 82°–83° C. during 8 hours. The pressure reading on the pressure gauge reaches a peak value of 1.4 bars.

A thick liquid product is thus obtained which, after an approximately 12-hour ageing, is dried inside a rotary dryer, under vacuum (about 60 torr) and is then calcined in air at 550° C. for about 8 hours.

When analysed by powder x-ray diffractometry, the calcined solid product results to be amorphous; it displays a BET specific surface area of 682 m$^2$/g, and a pore volume of 0.537 cm$^3$/g.

In following Table 3, the data are reported of catalytic activity in propylene oligomerization reaction, carried out by operating with a WHSV value of 4 h$^{-1}$, and under a 35-bar pressure.

TABLE 3

| T.O.S. | Temperature (°C.) | Conversion (%) |
|---|---|---|
| 20 | 150 | 87 |
| 115 | 150 | 67 |
| 158 | 150 | 60 |

EXAMPLE 4

In this Example, the process according to the present invention is carried out with the following molar ratios of the components of the reaction mixture:

| $SiO_2:Al_2O_3$ | = | 100 |
|---|---|---|
| TPA—OH:$SiO_2$ | = | 0.09 |
| $H_2O:SiO_2$ | = | 15 |

An amount of 302 g of water and 274 g of TPA-OH (used an a solution at 14% by weight in water) are charged to a flask of 2 liters of capacity, equipped with a reflux condenser.

When temperature reaches the value of 50°–60° C. 8 g of Al(OiPr)$_3$ is added. When aluminum salt is dissolved, the temperature is increased up to 98° C., heating is discontinued and 416 g of TEOS is added. When the hydrolysis reaction is complete, temperature begins to spontaneously decrease: now, heating is started up again, so as to keep the reaction mixture at the temperature of 82°–83° C. during 1 hour and 45 minutes.

After being submitted to a 20-hour ageing, the product is discharged from the flask, is dried inside a rotary dryer and in a vacuum oven and is then calcined in air at 550° C. for about 8 hours.

When analysed by powder x-ray diffractometry, the calcined solid product results to be amorphous; it displays a BET specific surface area of 804 m$^2$/g, and a specific pore volume of 0.773 cm$^3$/g. The result from the porosimetric analysis is reported in FIG. 2.

In following Table 4 the data are reported of catalytic activity in propylene oligomerization reaction, carried out by operating with a WHSV value of 4 h$^{-1}$, and under a 35-bar pressure.

TABLE 4

| T.O.S | Temperature (°C.) | Conversion (%) |
|---|---|---|
| 25 | 150 | 88 |
| 54 | 150 | 82 |
| 134 | 150 | 78 |

EXAMPLE 5

In this Example, the process is carried out with the following molar ratios of the components of the reaction mixture:

| $SiO_2:Al_2O_3$ | = | 100 |
|---|---|---|
| TBA—OH/$SiO_2$ | = | 0.09 |
| $H_2O:SiO_2$ | = | 15 |

** TBA=Tetrabutyl ammonium hydroxide, supplied as a 18.9% solution, by weight, in water.

The process is carried out in a reactor equipped with reflux condenser, by operating according to the same modalities as of Example 4, with the following amounts of reactants:

| water | = | 186.5 g |
|---|---|---|
| TBA—OH | = | 103 g |
| Al(OiPr)$_3$ | = | 4 g |
| TEOS | = | 208 g |

The resulting solid product is amorphous on x-ray analysis; it displays a BET surface area of 837 m$^2$/g and a pore volume of 0.737 cm$^3$/g.

EXAMPLE 6

The process is carried out in a reactor equipped with reflux condenser, similarly to preceding Example 4, with the difference that ethyl alcohol (EtOH) is added, previously dissolved in TEOS is added with a molar ratio of:

EtOH:TEOS=4.

The solid product results to be amorphous on x-ray analysis, and shows a BET surface area of 674 m$^2$/g and a pore volume of 0552 cm$^3$/g.

Figure 3:
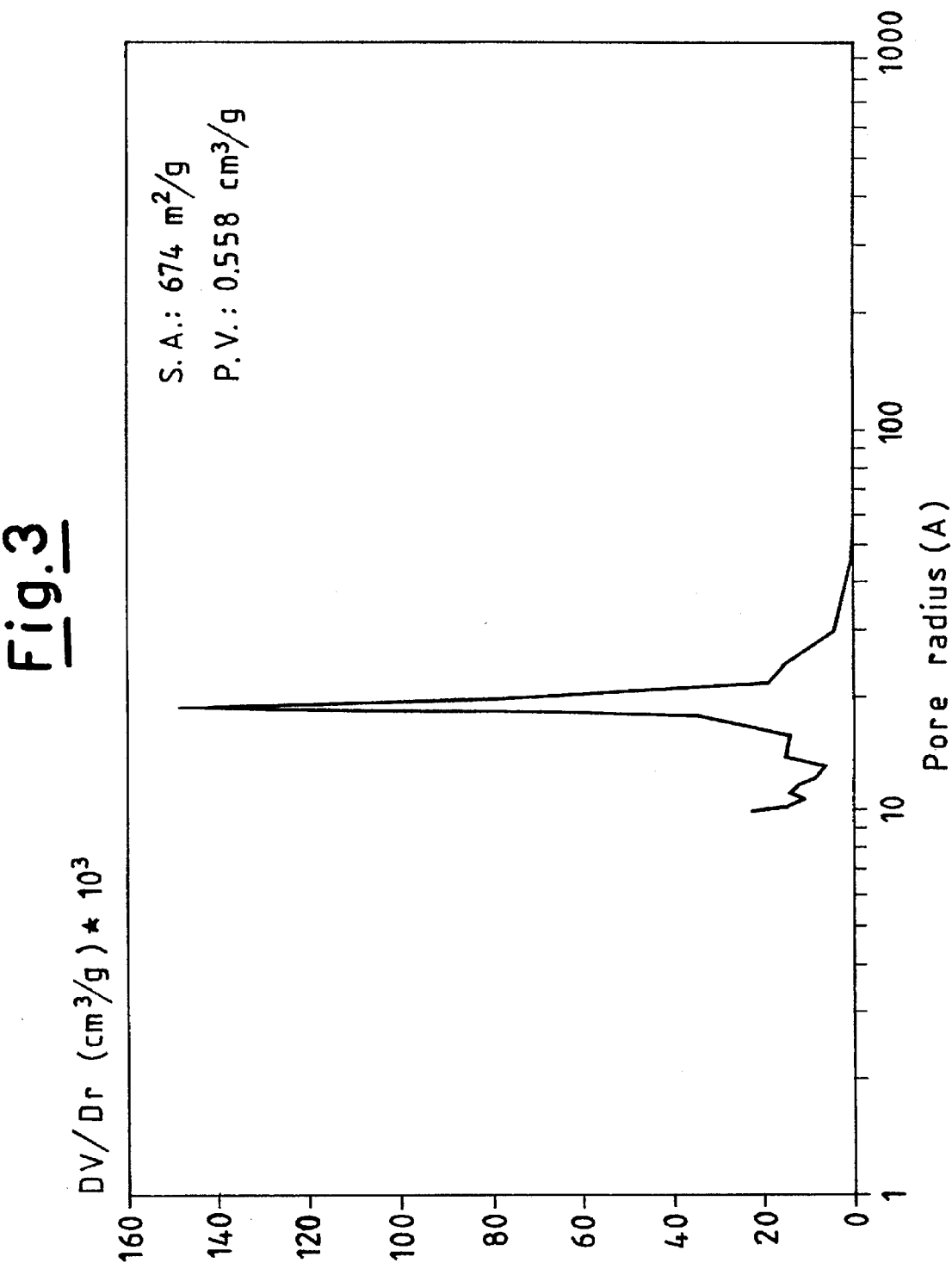
Figure 4:
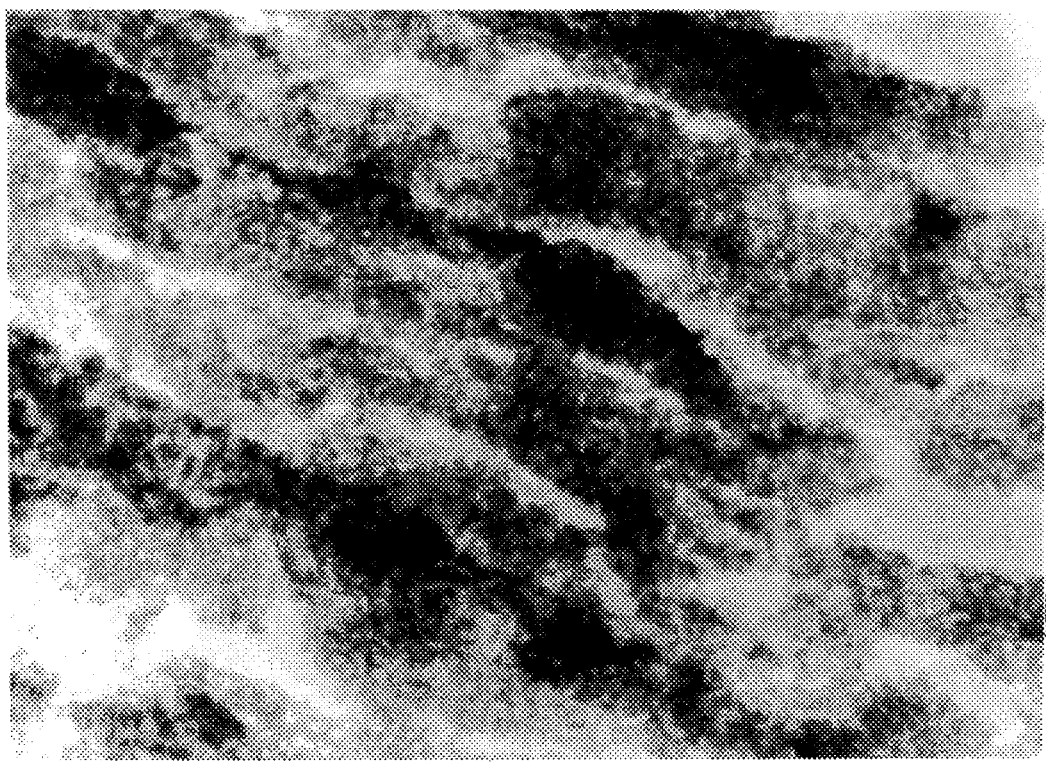

In accompanying FIG. 4 the microphotograph obtained by transmission electron microscope is reported. A regular distribution and a pore uniformity in sample particles are evidenced. Such an observation is consistent with the porosimetric analysis reported in accompanying FIG. 3.

Figure 2:
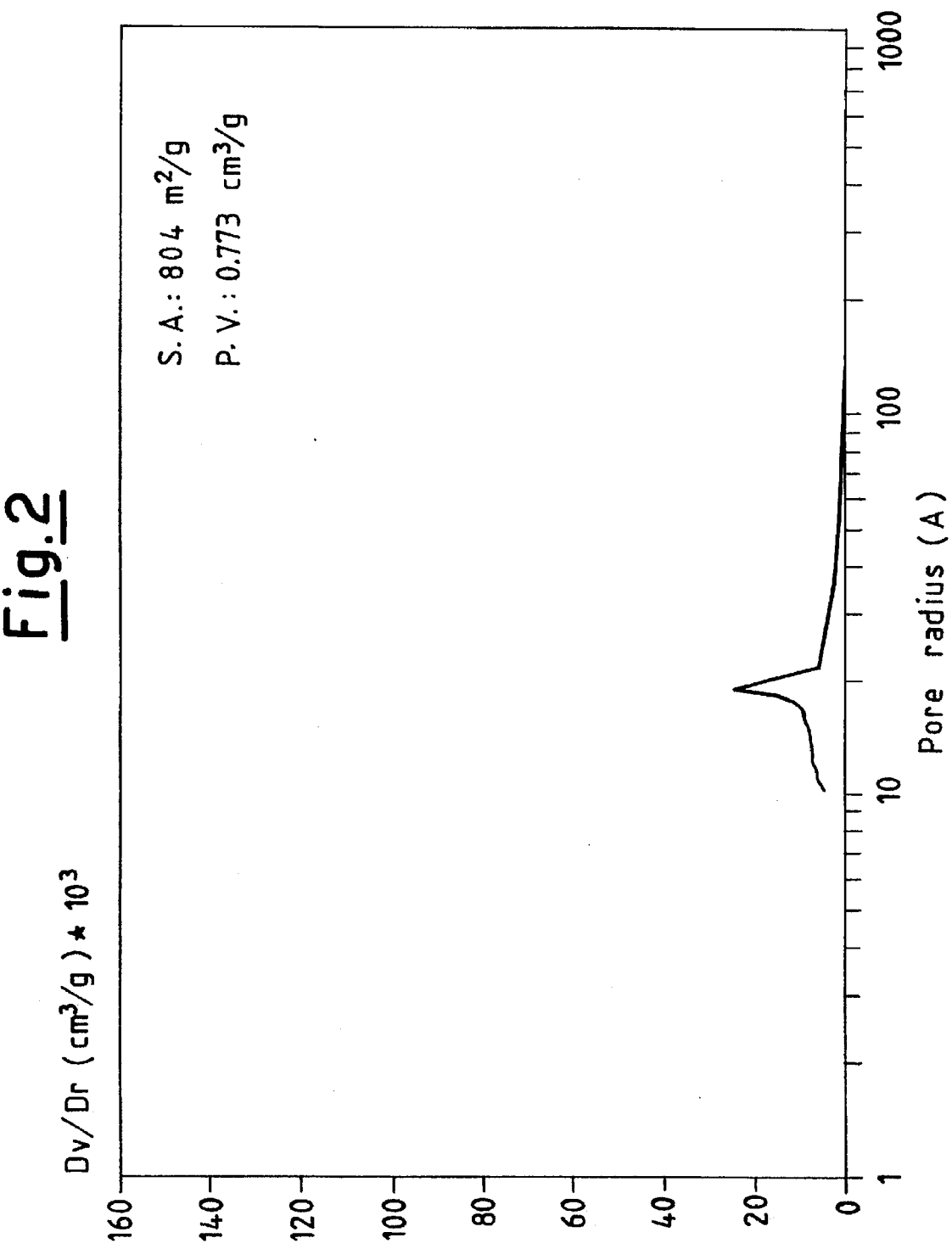

From the charts reported in FIGS. 1–3, one will observe that the samples prepared according to the process of the present Application display an extremely narrow and regular distribution of pore size, with pore radius being of about 20 Ångstrom. The presence of such pores is clearly visible when the product is viewed under transmission electron microscope (TEM). These pores result to be regular as regards their size, and distributed throughout amorphous silicoalumina particles.

EXAMPLE 7

Comparison Example

The test is run according to such modalities as disclosed in U.S. Pat. No. 5,049,536; by charging the reactant a beaker, in the following molar proportions:

| | | |
|---|---|---|
| SiO$_2$:Al$_2$O$_3$ | = | 50 |
| TPA—OH:SiO$_2$ | = | 0.09 |
| H$_2$O:SiO$_2$ | = | 15 |

**TPA=tetrapropyl ammonium hydroxide, supplied as a solution at 13.35% by weight in water.

An x-ray analysis amorphous solid product is obtained, which displays a BET surface area of 672 m$^2$/g and a pore volume of 0.454 cm$^3$/g.

In following Table 5, the data are reported of catalytic activity displayed by the product in propylene oligomerization reaction carried out by operating with a WHSV value of 4 h$^{-1}$ and under a 35-bar pressure.

TABLE 5

| T.O.S. | Temperature (°C.) | Conversion (%) |
|---|---|---|
| 41 | 120 | 59 |
| 162 | 150 | 50 |
| 210 | 170 | 49 |

EXAMPLE 8

Figure 5:
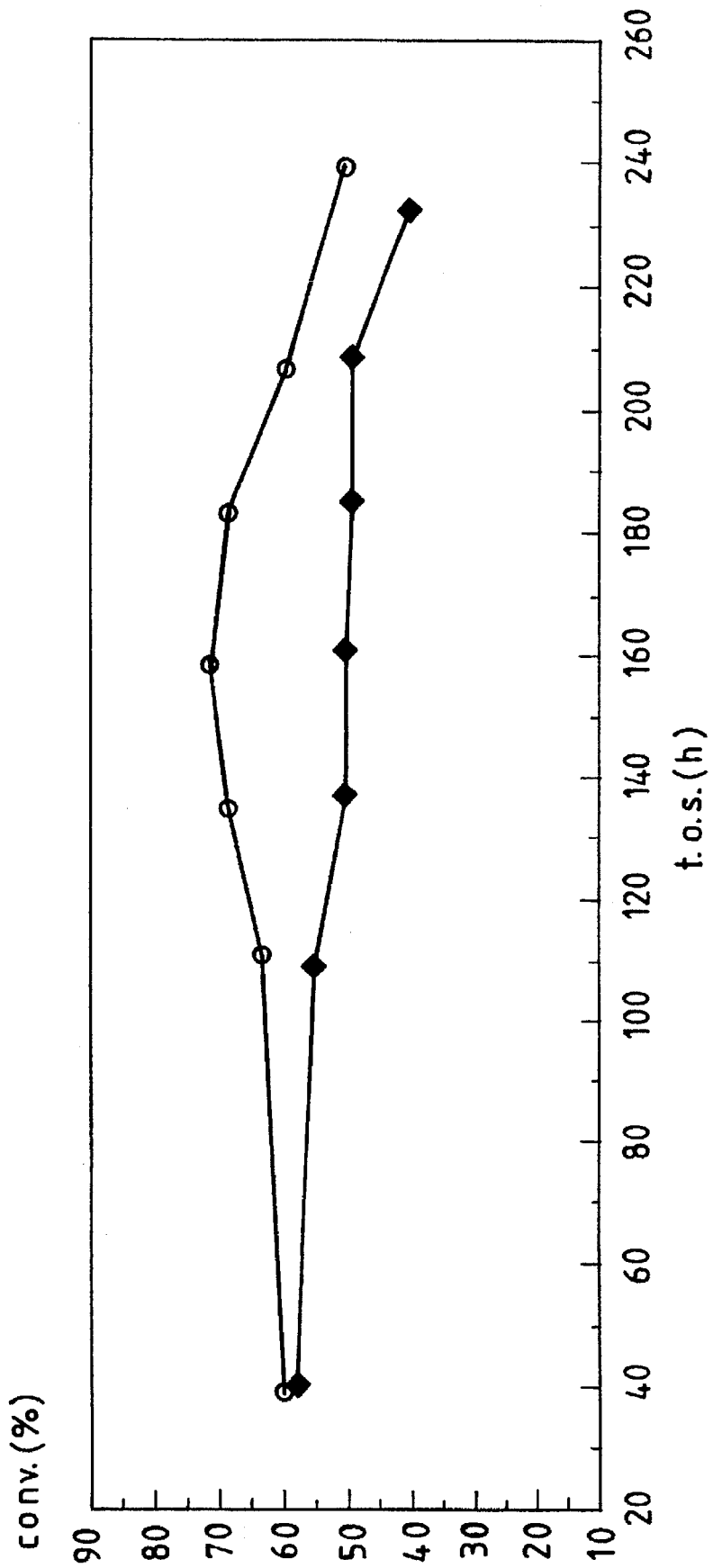

In accompanying FIG. 5 two life tests are compared, which were out: the carried first one with the sample from Example 4, the other one with the sample from Comparison Example 7.

The characteristics and operating modalities in the test runs were as follows:
catalyst shape: pelletized catalyst;
catalyst size: 20–40 mesh;
reactor type: fixed bed reactor;
feed: propylene/propane (70:30 by weight) mixture;
reactor temperature from 120° C. to 180° C.;
reactor temperature: 38 bars;
weight hourly space velocity WHSV: 4 g of propylene per active phase gram per hour;
total reaction time: about 240 hours.

The tests were carried out by stepwise increasing the reaction temperature, by 10° C. each time (about every 24 hours) in order to compensate for the conversion decrease due to catalyst deactivation.

As one will see from FIG. 5, silicoalumina from Example 4 ("--o--o--" line) constitutes a catalyst with improved performance over silicoalumina from Comparison Example 7 ("--*--*--" line).

In particular, the value of productivity (understood as grams of oligomer produced per each gram of active phase) of the catalyst from Example 4 is of 510 g/g, whilst for catalyst from Comparison Example 7, it is of 400 g/g.

We claim:

1. A method comprising propylene oligomerization in the presence of a silica-alumina gel catalyst, wherein said catalyst is an amorphous silica-alumina gel having a surface area of at least 500 m$^2$/g and a molar ratio of SiO$_2$:Al$_2$O$_3$ of at least 30:1, wherein said catalyst is prepared by (1) hydrolyzing and gelling an aqueous reaction medium comprising a tetra-(C$_2$-C$_5$)-alkyl ammonium hydroxide, an aluminum tri-(C$_2$-C$_4$)-alkoxide and a tetra-(C$_1$-C$_5$)-alkyl orthosilicate at a temperature equal to or higher than the boiling temperature at atmospheric pressure of any alcohol produced during said hydrolyzing and gelling steps, without substantially removing said alcohol from said reaction media to produce a gel; and (2) drying and firing said gel.

2. The method of claim 1, wherein said tetra-(C$_2$-C$_5$)-alkyl ammonium hydroxide is selected from the group consisting of tetrapropyl ammonium hydroxide, tetraisopropyl ammonium hydroxide and tetrabutyl ammonium hydroxide, said aluminum tri-(C$_2$-C$_4$)-alkoxide is selected from the group consisting of aluminum tripropoxide and aluminum triisopropoxide, and said tetra-(C$_1$-C$_5$)-alkyl orthosilicate is tetraethyl orthosilicate.

3. The method of claim 1, further comprising prior to said hydrolyzing step, preparing an aqueous solution containing said tetra-(C$_2$-C$_5$)-alkyl ammonium hydroxide and said aluminum tri-(C$_2$-C$_4$)-alkoxide and adding said tetra-(C$_1$-C$_5$)-alkyl orthosilicate to said solution at a temperature lower than the temperature of said hydrolyzing, wherein the molar ratio SiO$_2$:Al$_2$O$_3$ is 30:1 to 500:1, the molar ratio tetra-(C$_2$-C$_5$)-alkyl ammonium hydroxide:SiO$_2$ is 0.05:1 to 0.2:1 and the molar ratio H$_2$O:SiO$_2$ is 5:1 to 40:1.

4. The method of claim 3, wherein said hydrolyzing and gelling is conducted at a temperature of about 65° C. up to about 110° C.

5. The method of claim 1, wherein said aqueous reaction medium contains an alcohol in an amount up to a maximum molar ratio alcohol:SiO$_2$ of 8:1.

6. The method of claim 5, wherein said alcohol is ethanol.

7. The method of claim 1, wherein said hydrolyzing and gelling is conducted for a time ranging from 10 minutes to 3 hours.

8. The method of claim 7, wherein said hydrolyzing and gelling is conducted for a time ranging from 1–2 hours.

9. The method of claim 1, further comprising aging said gel at room temperature for 1–24 hours.

10. The method of claim 1, further comprising removing said alcohol produced during said hydrolyzing and gelling step from said gel and then vacuum drying said gel to produce a dried gel, and firing said dried gel in an oxidizing atmosphere at a temperature in the range from 500° to 700° C. for a time ranging from 4 to 20 hours.

11. The method of claim 10, wherein said firing is at a temperature of 500°–600° C. for a time ranging from 6–10 hours.

12. The method of claim 1, wherein said hydrolyzing and gelling are conducted at a temperature of 82° C. to about 110° C.

13. The method of claim 12, wherein said hydrolyzing and gelling is conducted at a temperature of 88° C. to about 110° C.

14. The method of claim 1, wherein said dried and fired gel has an average pore radius from 10 to about 20Å.

15. The method of claim 1, wherein said dried and fired gel has a surface area of from 600–850 $m^2/g$.

* * * * *